(12) United States Patent
Saito

(10) Patent No.: US 12,307,169 B2
(45) Date of Patent: May 20, 2025

(54) METHOD AND APPARATUS FOR ANALYZING SENSITIVITY OF AUTOMOTIVE BODY PARTS AND METHOD FOR DETERMINING MATERIAL PROPERTY OF AUTOMOTIVE BODY PARTS

(71) Applicant: JFE STEEL CORPORATION, Tokyo (JP)

(72) Inventor: Takanobu Saito, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 882 days.

(21) Appl. No.: 17/272,846

(22) PCT Filed: Jun. 11, 2019

(86) PCT No.: PCT/JP2019/023024
§ 371 (c)(1),
(2) Date: Mar. 2, 2021

(87) PCT Pub. No.: WO2020/070922
PCT Pub. Date: Apr. 9, 2020

(65) Prior Publication Data
US 2021/0357544 A1    Nov. 18, 2021

(30) Foreign Application Priority Data

Oct. 5, 2018    (JP) .................................. 2018-189612

(51) Int. Cl.
*G06F 30/00* (2020.01)
*G01M 1/12* (2006.01)
(Continued)

(52) U.S. Cl.
CPC ............. *G06F 30/15* (2020.01); *G01M 1/122* (2013.01); *G01M 17/007* (2013.01); *G01N 9/00* (2013.01);
(Continued)

(58) Field of Classification Search
CPC ...... G06F 30/15; G06F 30/23; G06F 2111/04; G01M 1/122; G01M 17/007; G01N 9/00; G07C 5/0808; G16C 60/00
See application file for complete search history.

(56) References Cited

U.S. PATENT DOCUMENTS 5,481,465 A * 1/1996 Itoh ......................... G06T 17/20
700/118
5,729,463 A * 3/1998 Koenig ................... B23K 11/11
703/2
(Continued)

FOREIGN PATENT DOCUMENTS

CN    106844874 A    6/2017
CN    107330172 A    11/2017
(Continued)

OTHER PUBLICATIONS

CN 1068844874A in view of English Translation (Year: 2016).*
(Continued)

*Primary Examiner* — Ian Jen
(74) *Attorney, Agent, or Firm* — Oliff PLC

(57) ABSTRACT

A method for analyzing sensitivity of automotive body parts with respect to an automotive body performance of an automotive body including the automotive body parts, the method being executed by a computer and including: acquiring an automotive body model including the automotive body parts modelled with elements; setting: an objective condition related to an automotive body performance of the automotive body model; a constraint condition related to a volume of the automotive body model; and a loading condition to be imposed on the automotive body model; obtaining sensitivities of respective elements that satisfies the objective condition under the loading condition and the constraint condition; and calculating sensitivities of each of (Continued)

the automotive body parts based on the sensitivities of the respective elements.

12 Claims, 12 Drawing Sheets

(51) Int. Cl.
  *G01M 17/007* (2006.01)
  *G01N 9/00* (2006.01)
  *G06F 30/15* (2020.01)
  *G07C 5/08* (2006.01)
  *G16C 60/00* (2019.01)
  *G06F 30/23* (2020.01)
  *G06F 111/04* (2020.01)

(52) U.S. Cl.
  CPC ........... *G07C 5/0808* (2013.01); *G16C 60/00* (2019.02); *G06F 30/23* (2020.01); *G06F 2111/04* (2020.01)

(56) References Cited

U.S. PATENT DOCUMENTS

| | | | | |
|---|---|---|---|---|
| 6,195,625 B1* | 2/2001 | Day | ........................ | G06T 19/20 703/7 |
| 6,212,486 B1* | 4/2001 | Huang | ..................... | G06F 30/23 703/2 |
| 6,385,564 B1* | 5/2002 | Brown | .................. | G01M 7/027 703/2 |
| 6,510,357 B1* | 1/2003 | Naik | ....................... | G05B 17/02 700/98 |
| 6,941,250 B1 | 9/2005 | Nishiwaki et al. | | |
| 7,243,055 B2* | 7/2007 | Chen | ........................ | G06F 30/20 703/2 |
| 7,657,412 B2* | 2/2010 | Honma | ................... | G06F 30/00 703/1 |
| 7,908,123 B2* | 3/2011 | Maebayashi | ........... | G06Q 10/06 703/1 |
| 8,032,343 B2* | 10/2011 | Cai | ......................... | G06F 30/15 703/7 |
| 8,219,365 B2* | 7/2012 | Allen | ....................... | G06F 30/15 703/2 |
| 8,378,254 B2* | 2/2013 | Gagliano | ................ | F16F 15/02 219/121.64 |
| 9,098,673 B2* | 8/2015 | Fonseka | .................. | G06F 30/15 |
| 2006/0283015 A1* | 12/2006 | Lowe | ...................... | B62D 65/02 29/428 |
| 2010/0244472 A1* | 9/2010 | Gonin | ...................... | B60R 19/12 293/133 |
| 2010/0262406 A1 | 10/2010 | Goel et al. | | |
| 2011/0066265 A1* | 3/2011 | Gagliano | ................ | F16F 15/02 700/95 |
| 2011/0115241 A1* | 5/2011 | Gonin | ...................... | B60R 19/12 293/146 |

FOREIGN PATENT DOCUMENTS

| | | |
|---|---|---|
| JP | H04-096182 A | 3/1992 |
| JP | 2002-183220 A | 6/2002 |
| JP | 2003-285735 A | 10/2003 |
| JP | 2008-040528 A | 2/2008 |
| JP | 2009-199358 A | 9/2009 |
| JP | 2010-250818 A | 11/2010 |

OTHER PUBLICATIONS

A study of optimization for auto parts and structures using inertia relief, 11th world congress on structural and multidisciplinary optimization Jun. 2015 (Year: 2015).*
Sep. 12, 2023 Office Action issued in Chinese Patent Application No. 201980065155.4.
Wang Zhenhu et al., "Size Optimization on Main Cross-sections of Body-in-white Based on Conceptual Model for Car Body", Automotive Engineering vol. 40 No. 8, (2018), pp. 904-911.
Jul. 23, 2019 International Search Report issued in International Patent Application No. PCT/JP2019/023024.
Nov. 8, 2021 Extended European Search Report issued in European Patent Application No. 19869710.4.
Jul. 1, 2022 Office Action issued in Korean Patent Application No. 10-2021-7005359.
Mar. 30, 2024 Office Action issued in Chinese Application No. 201980065155.4 (with partial translation).
Feb. 25, 2025 Office Action issued in European Patent Application No. 19869710.4.

* cited by examiner

FIG.4
(a)
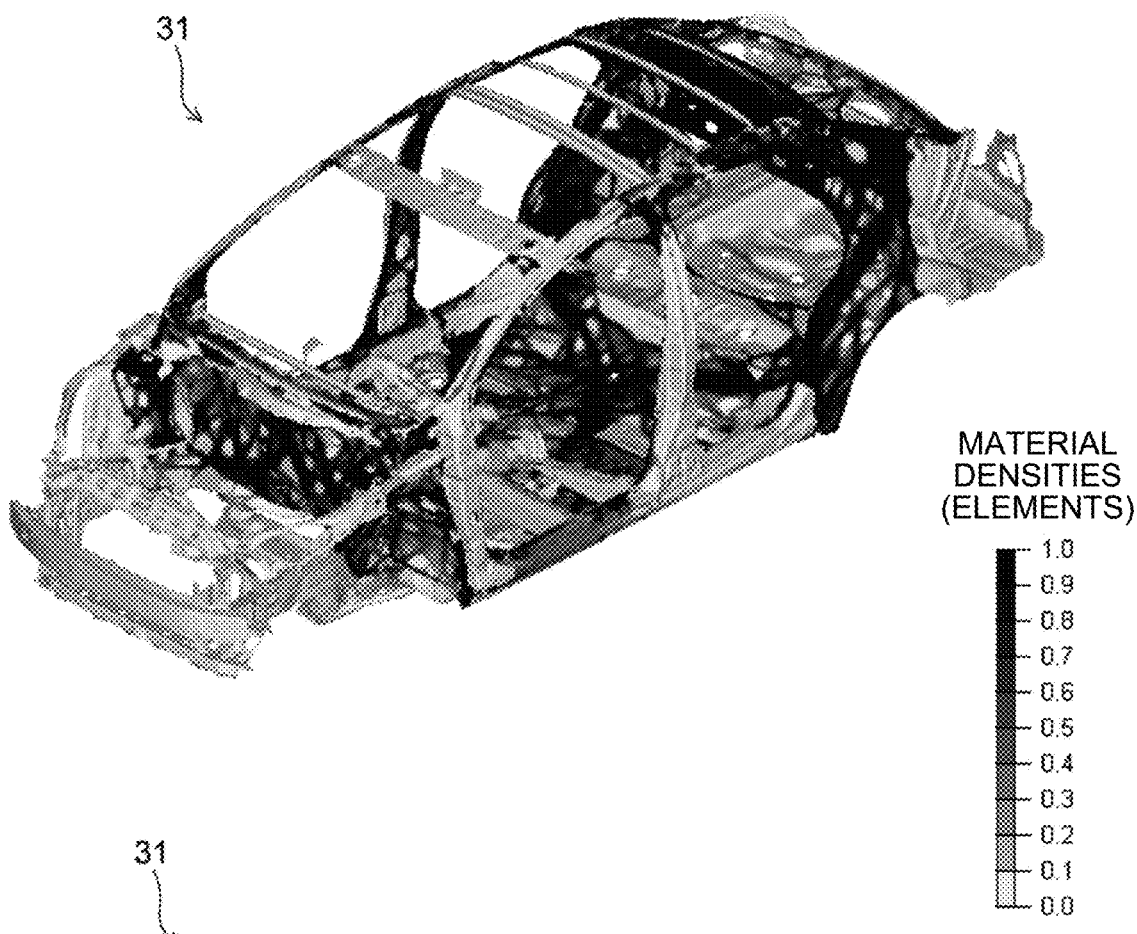
(b)
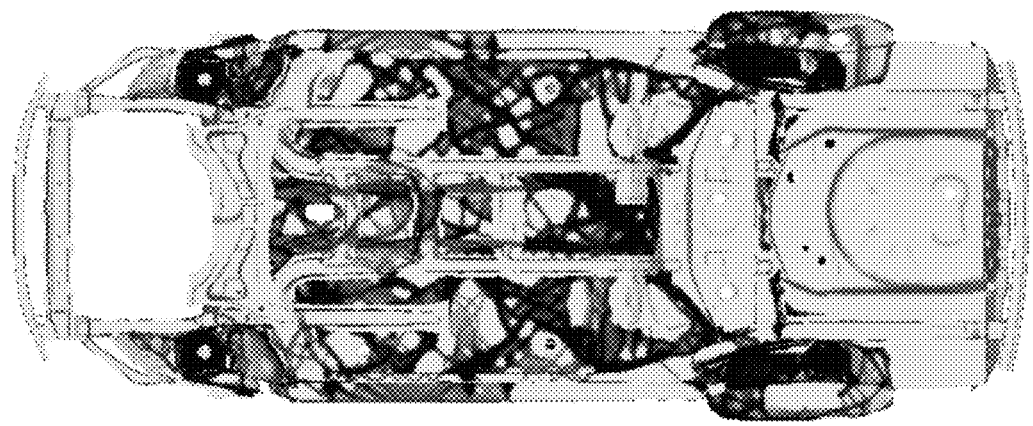

(a)          (b)

(a)          (b)

FIG.7
(a)
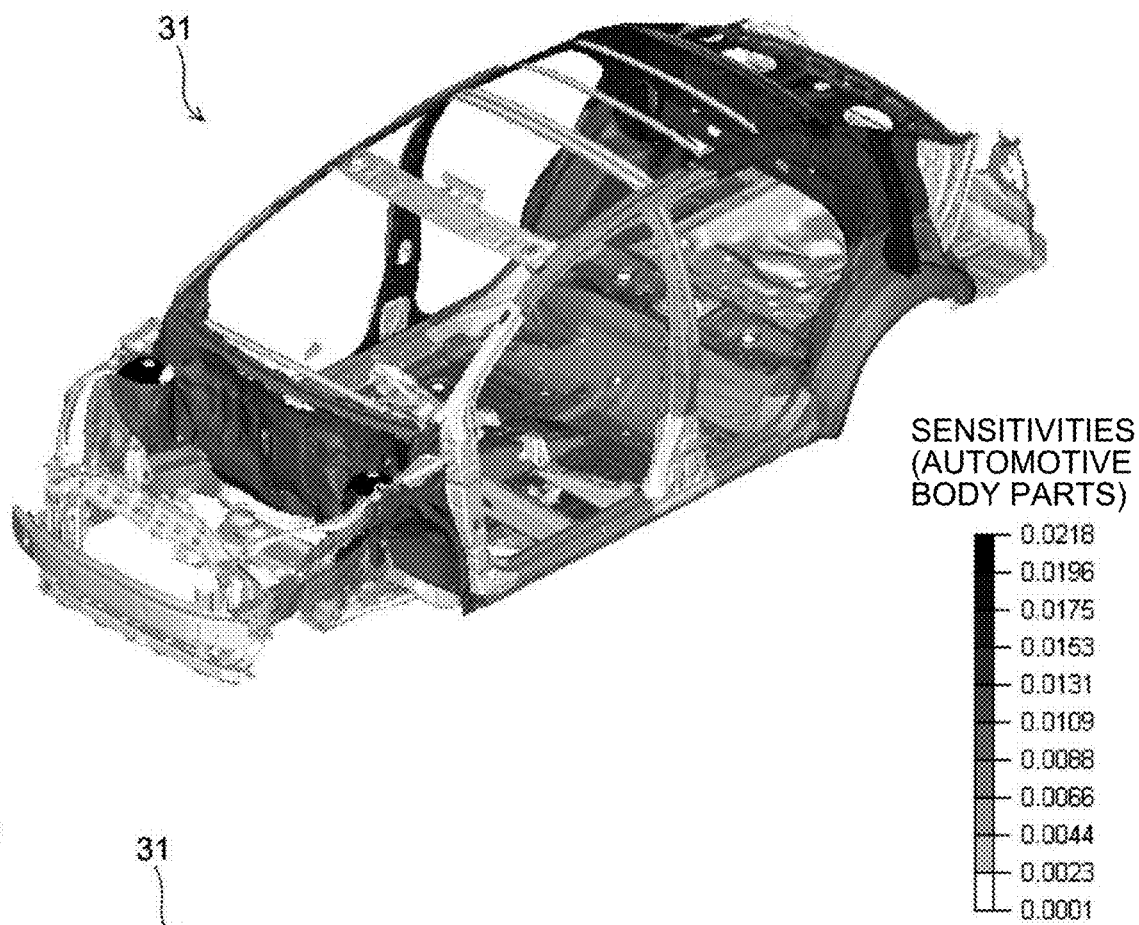
(b)
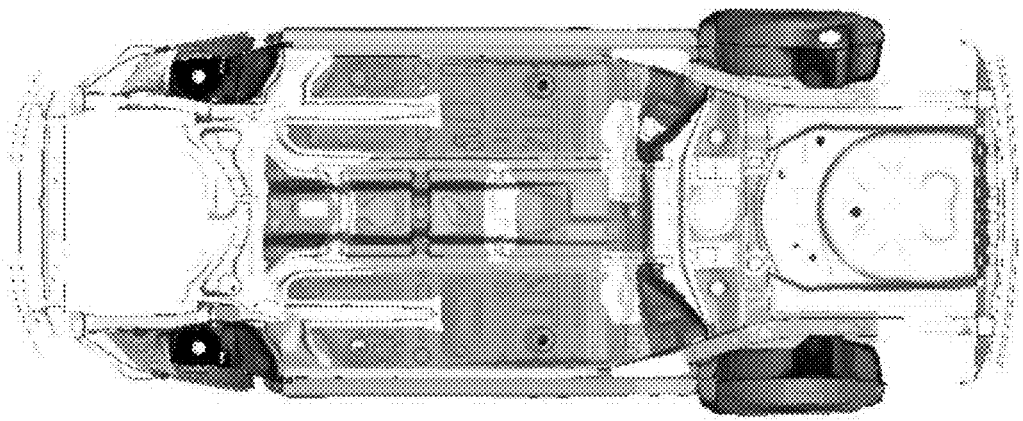

FIG.8
(a)
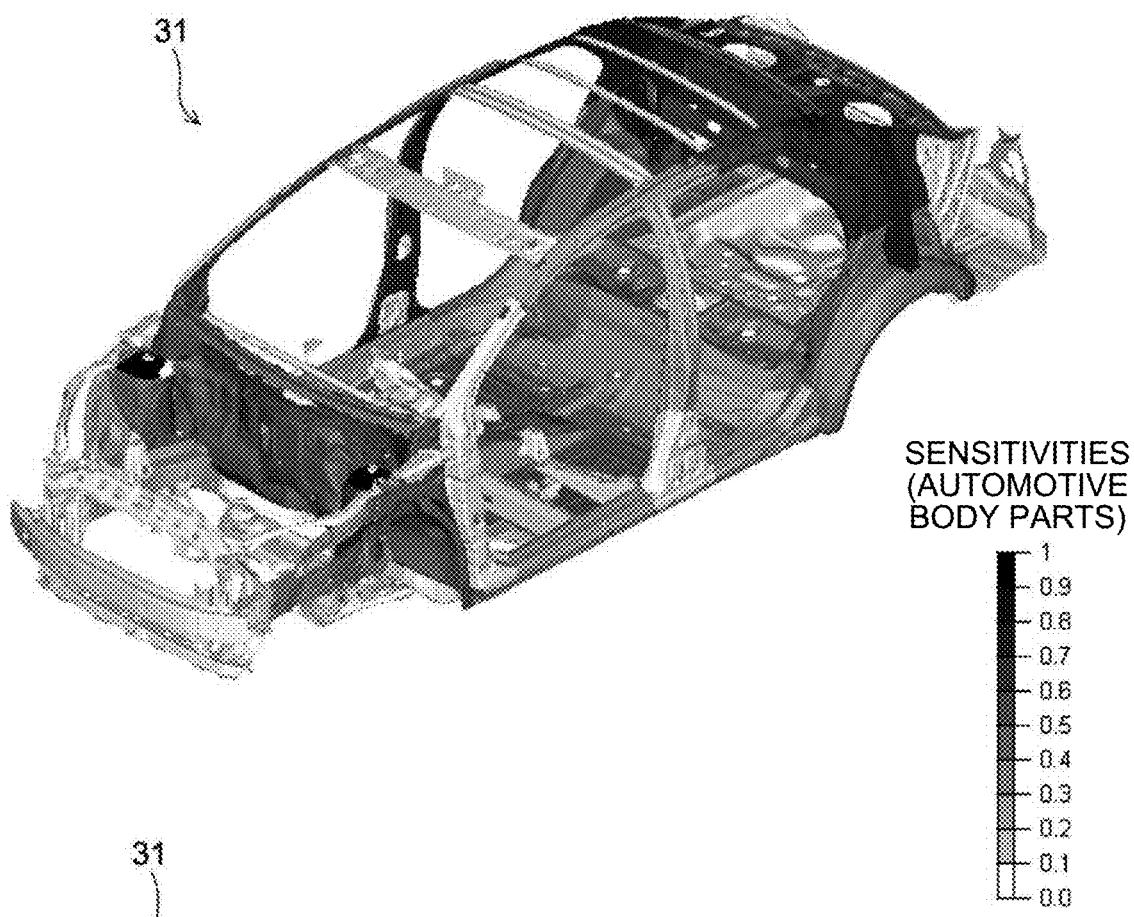
(b)
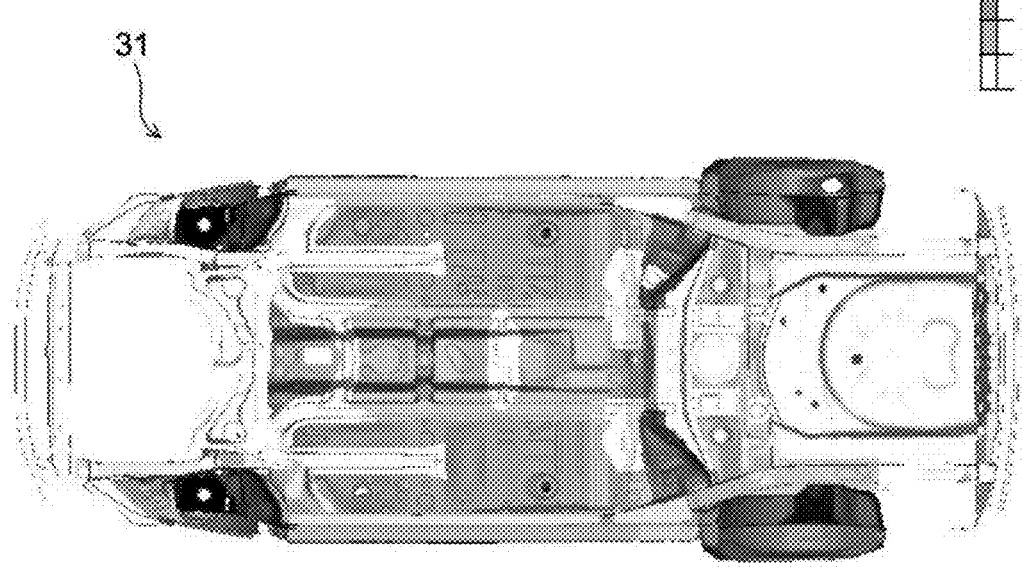

FIG.10
(a)
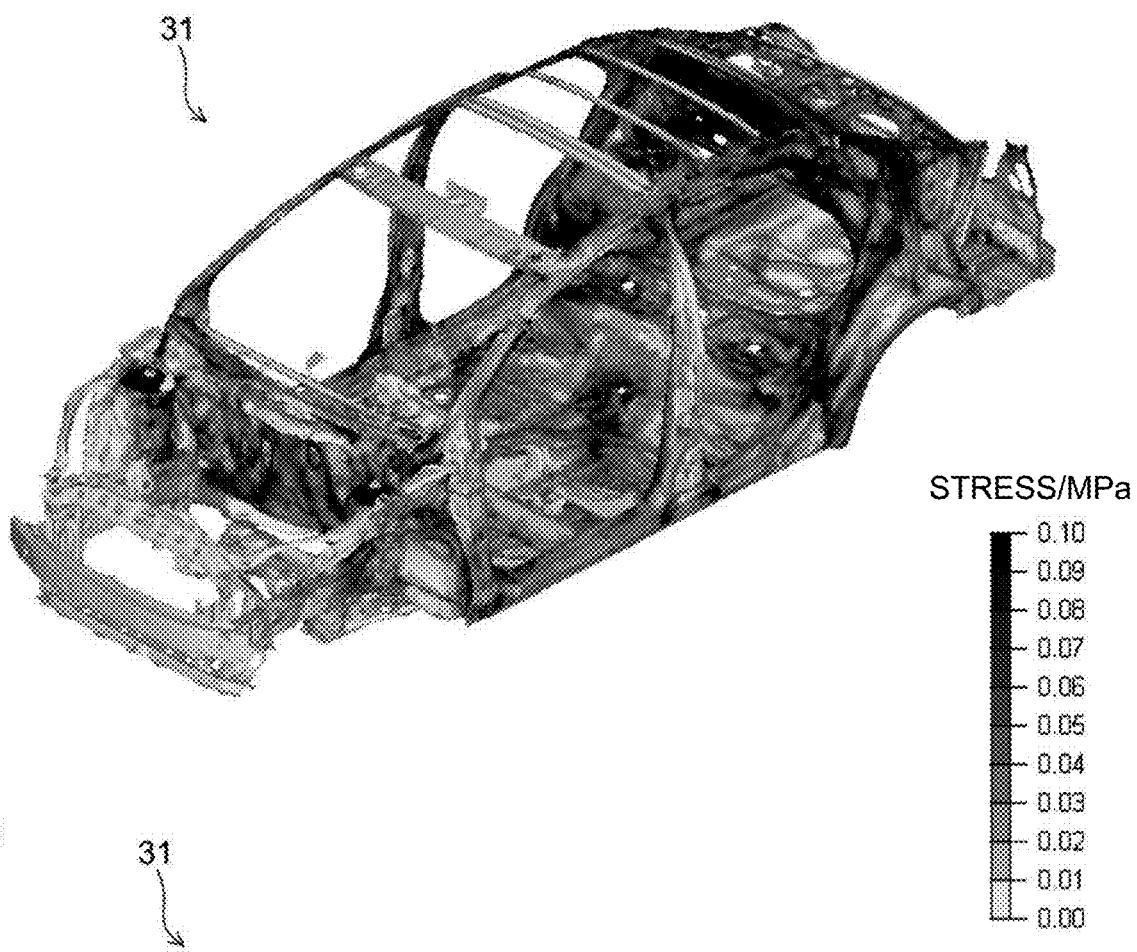
(b)
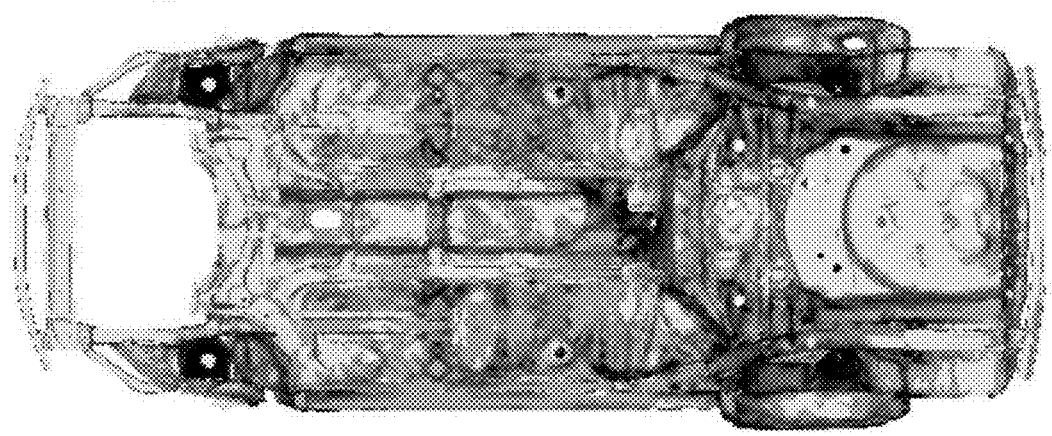

FIG.12
(a)
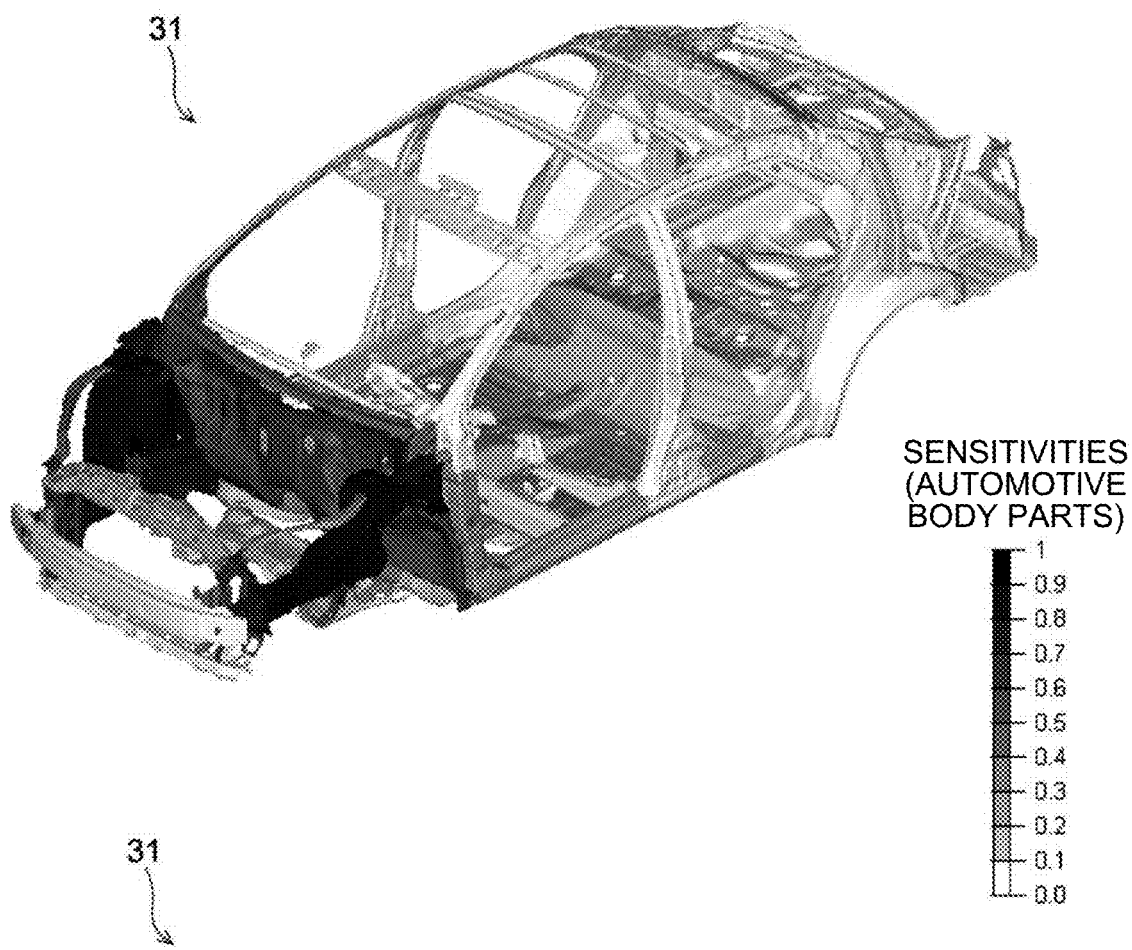
(b)
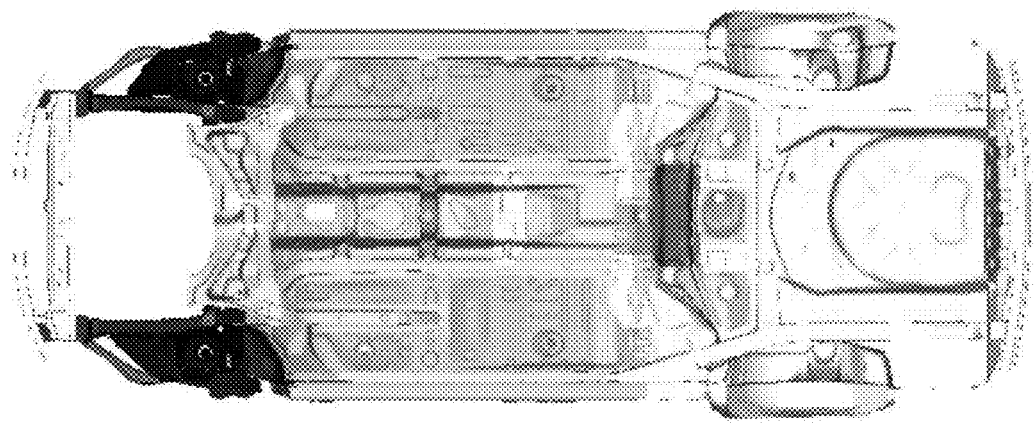

FIG.13
(a)
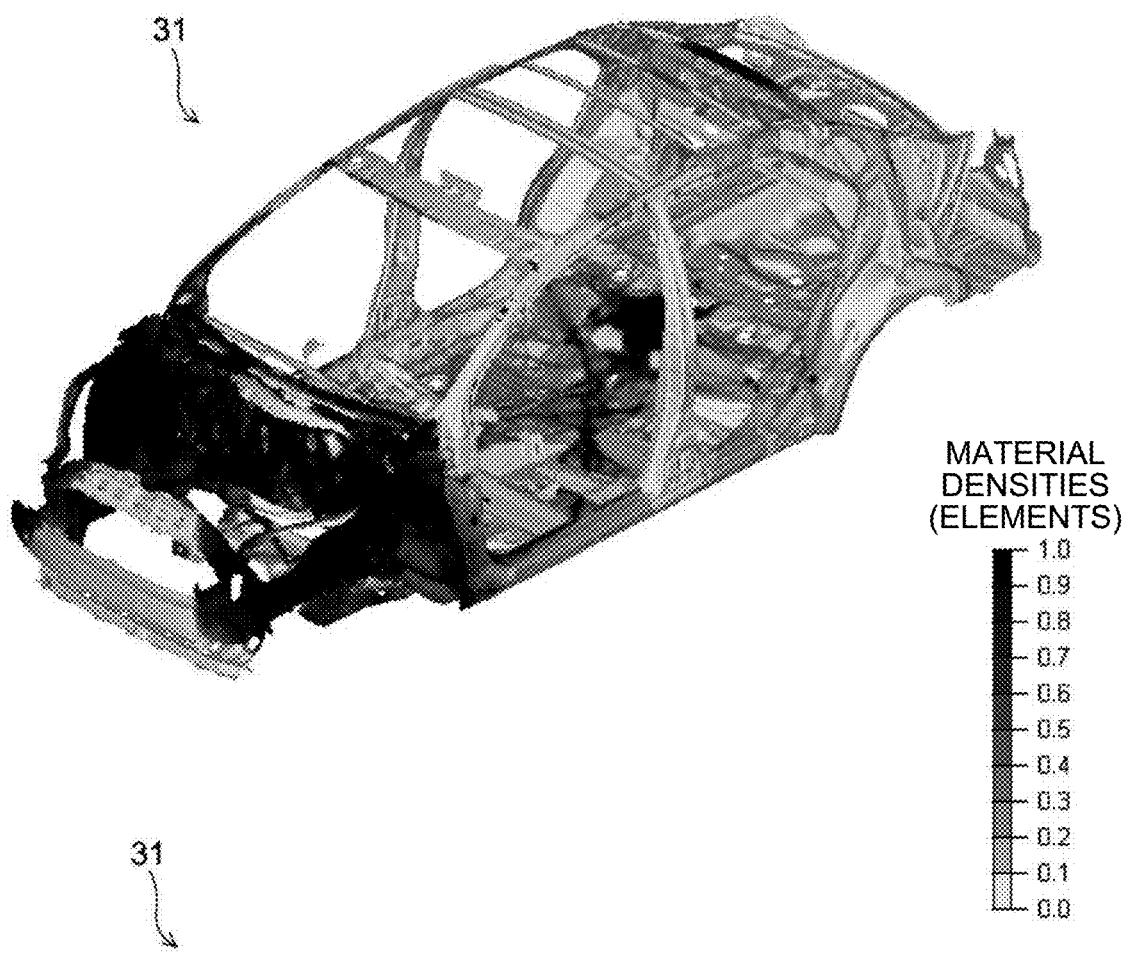
(b)
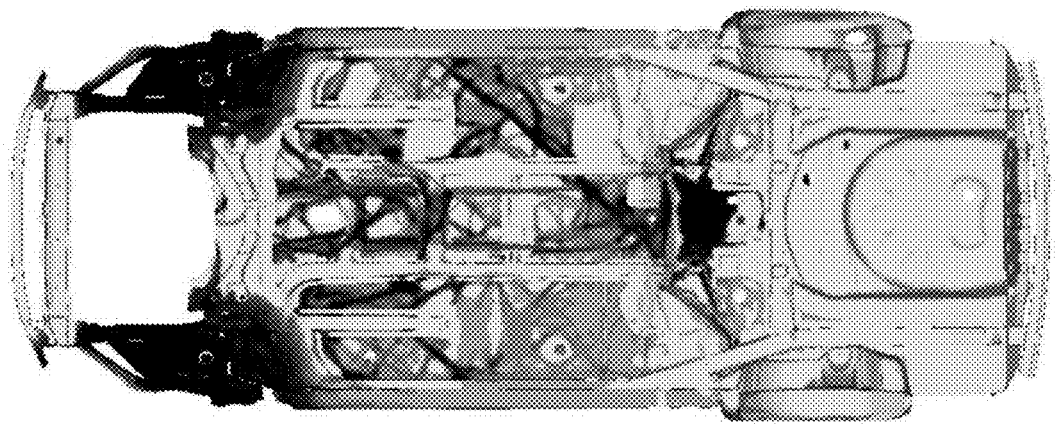

FIG.14
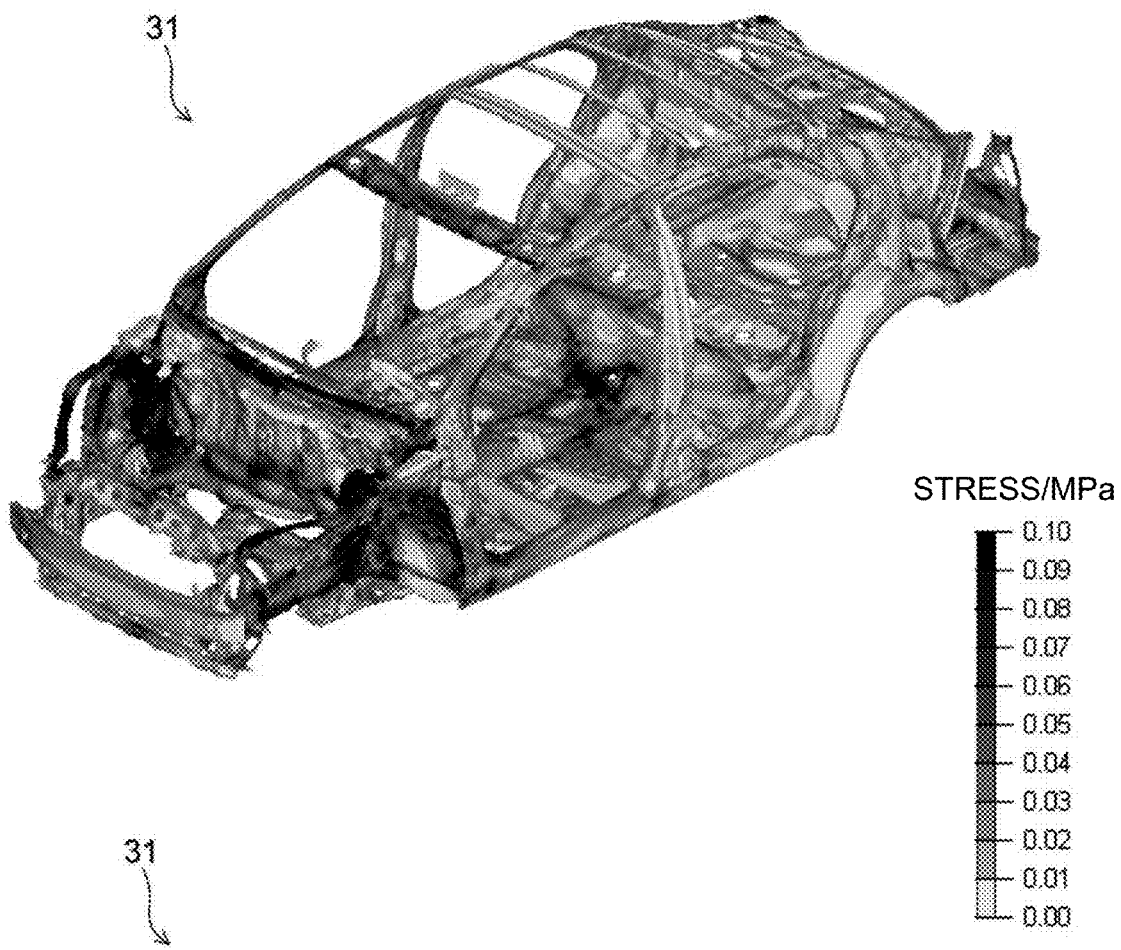
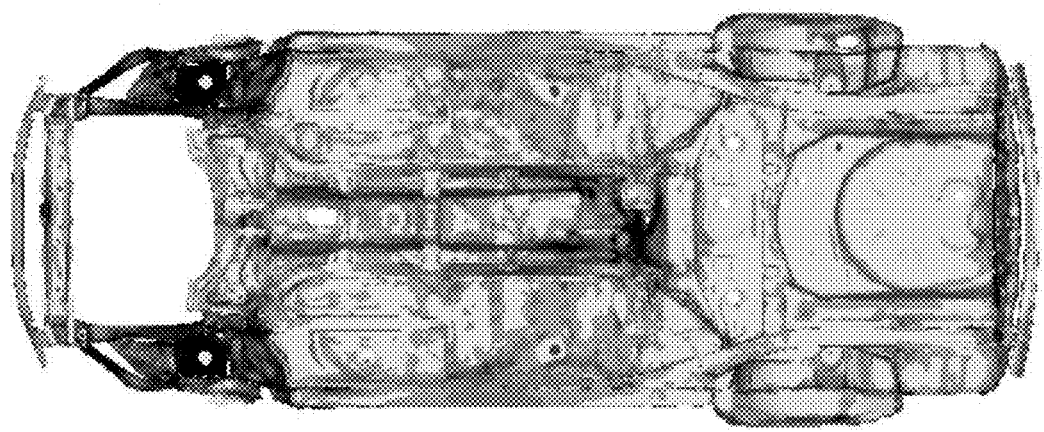

METHOD AND APPARATUS FOR ANALYZING SENSITIVITY OF AUTOMOTIVE BODY PARTS AND METHOD FOR DETERMINING MATERIAL PROPERTY OF AUTOMOTIVE BODY PARTS

FIELD

The present invention relates to a method and apparatus for analyzing a sensitivity (sensitivity analysis) of automotive body parts with respect to an automotive body performance, and a method for determining a material property of the automotive body parts.

BACKGROUND

Recently, in the automotive industry, in particular, the weight reductions of automotive bodies have been promoted to address environmental issues, and computer-aided engineering (CAE) has become an essential technology in designing automotive bodies. In a CAE analysis, analyses such as a stiffness analysis, a crashworthiness analysis, and a vibration analysis are carried out, and such analyses largely contribute to evaluating the performance of the automotive bodies. Furthermore, it has been known that, in the CAE analysis, it is not only possible to make evaluations of automotive bodies, but also to improve various performances of automotive bodies, and to achieve weight reductions of automotive bodies, using optimization technologies such as a mathematical optimization, a thickness optimization, a shape optimization, and a topology optimization using the analysis results. As one example of the optimization technologies, Patent Literature 1 discloses a topology optimization method for a component having a complex structure.

CITATION LIST

Patent Literature

Patent Literature 1: Japanese Patent Application Laid-open No. 2010-250818

SUMMARY

Technical Problem

When the topology optimization is to be performed as an optimization technology for improving the performance of an automotive body, or for reducing the weight of an automotive body, for example, it is necessary to set a design space where the optimization analysis is to be performed, to a part of the automotive body. An effective method for determining the part where the design space is to be set is to figure out an important part that significantly contributes to the performance of the automotive body, and to set the design space based on the important part thus figured out. Some examples of the method include a method for using a part where a high stress is generated in the automotive body, a method for using a part where a large deformation takes place, and a method for obtaining how much an automotive body part contributes to the automotive body performance by changing only the thickness of the automotive body part.

However, with the methods for using a part of the automotive body where a high stress is generated, or where a large deformation takes place, the methods only clarify a part where a high stress is generated, or where a large deformation takes place, and such a part is not necessarily the part where the performance can be improved by providing some measure. As one example of a part where a deformation takes place is not necessarily the part where the performance can be improved by providing some measure, when a load is applied to a tip of a cantilever, the tip of the beam deforms by a large degree, but the location to be provided with a measure for suppressing the deformation is a constrained part at the base of the beam. In this manner, a part going through a high deformation is not necessarily the same as a part to be provided with a measure for improving the performance. Furthermore, with the method for obtaining how much an automotive body part contributes to the automotive body performance by changing the thickness of the automotive body part, although the method clarifies the automotive body part where the automotive body performance is changed by changing the thickness, but it clarifies only the contribution of the single automotive body part with the thickness changed, and it is not possible to obtain how much each of the automotive body parts contributes to the performance by changing the thicknesses of a plurality of automotive body parts at the same time, disadvantageously.

To address this issue, there has been a technique for applying a topology optimization to the shell elements of the entire automotive body, without defining a design space, and for using material densities (element densities) of the shell elements, the material densities being calculated in the topology optimization, as representations of sensitivities. With this approach, because the optimization is applied to satisfy an objective condition related to the automotive body performance, the shell elements that contribute to an improvement of the automotive body performance become clear by changing the thickness or the material property of the material (e.g., steel sheet) used in the automotive body. Furthermore, because the entire automotive body is to be optimized, it is also possible to obtain a contribution to the entire automotive body, instead of one automotive body part, unlike when only the thickness is changed. Because the sensitivity is obtained for each one of the shell elements, it is possible to obtain a part representing a small area corresponding to a shell element, and to clarify the position of the element in the automotive body. However, because an automotive body is an assembly of several hundred automotive body parts, and each automotive body part corresponds to a few thousands to a few hundred thousand shell elements, each of the automotive body parts has a sensitivity distribution. Hence, based on the analysis results of the sensitivities of the shell elements, it is difficult to distinguish which automotive body part is to be targeted, and to determine the sensitivity level of each of the automotive body parts, as illustrated in FIGS. 4 and 13, as will be described later, and it has been impossible to clarify the target automotive body part, disadvantageously. Furthermore, because the technology disclosed in Patent Literature 1 is pertinent to a mathematical operation and a physical analysis system, no solution is given to the issues described above.

The present invention is made in consideration of the issues described above, and an object of the present invention is to provide a method and apparatus for analyzing sensitivity of automotive body parts, and a method for determining material property of automotive body parts, being able of analyzing sensitivities of automotive body parts with respect to the automotive body performance, and of clarifying the automotive body part to be provided with a measure for improving the automotive body performance.

Solution to Problem

To solve the problem and achieve the object, a method for analyzing sensitivity of automotive body parts with respect to an automotive body performance of an automotive body including the automotive body parts, the method being executed by a computer, according to the present invention includes: an automotive body model acquisition step of acquiring the automotive body model including the automotive body parts modelled with elements; a sensitivity analysis step of: setting an objective condition related to an automotive body performance of the automotive body model, a constraint condition related to a volume of the automotive body model and a loading condition to be imposed on the automotive body model; and obtaining sensitivities of respective elements that satisfies the objective condition under the loading condition and the constraint condition; and automotive body parts sensitivity calculating step of calculating sensitivities of each of the automotive body parts based on the sensitivities of the respective elements.

Moreover, in the method for analyzing sensitivity of the automotive body parts according to the present invention, the sensitivity analysis step includes: calculating material densities of the respective elements satisfying the objective condition; and setting the calculated material densities of the respective elements as the sensitivities of the respective elements.

Moreover, in the method for analyzing sensitivity of the automotive body parts according to the present invention, the sensitivity analysis step includes standardizing values of the calculated sensitivities of each of the automotive body parts, to values between 0 and 1.

Moreover, in the method for analyzing sensitivity of the automotive body parts according to the present invention, the elements at the automotive body model acquisition step are shell elements, and the automotive body parts sensitivity calculating step includes: obtaining a sensitivity per element area by dividing the sensitivity of the respective elements by an area of the respective elements; and setting an integrated value obtained by adding up the sensitivity per element area for each of the automotive body parts or a value obtained by dividing the integrated value by number of elements included in each of the automotive body parts, as the sensitivity of each of the automotive body parts.

Moreover, in the method for analyzing sensitivity of the automotive body parts according to the present invention, the elements at the automotive body model acquisition step are rectangular elements, and at the automotive body parts sensitivity calculating step, the area of the element is obtained by: dividing each of the rectangular elements into two triangles each having three of the four nodal points of the rectangular element as vertices; calculating an area of each of the divided triangles; and taking a sum of the calculated areas of each of the divided triangles.

Moreover, in the method for analyzing sensitivity of the automotive body parts according to the present invention the elements at the automotive body model acquisition step are rectangular elements, and at the automotive body parts sensitivity calculating step, the area of the element is obtained by: dividing each of the rectangular elements into four triangles each having a center of gravity and two adjacent nodal points of the rectangular element as vertices; calculating an area of each of the divided triangles; and taking a sum of the calculated areas of each of the divided triangles.

Moreover, in the method for analyzing sensitivity of the automotive body parts according to the present invention, at the automotive body parts sensitivity calculating step, a highest sensitivity of the sensitivities of the elements making up each of the automotive body parts is set as a sensitivity of the each of the automotive body parts.

Moreover, a method for determining material property of automotive body parts according to the present invention is the method using the method for analyzing sensitivity of the automotive body parts according to the present invention, wherein material properties of the respective automotive body parts are determined based on the sensitivities obtained for the respective automotive body parts.

Moreover, an apparatus for analyzing sensitivity of automotive body parts with respect to an automotive body performance of an automotive body including the automotive body parts, according to the present invention includes: an automotive body model acquiring unit configured to acquire the automotive body model including automotive body parts modelled with elements; a sensitivity analyzing unit configured to: set an objective condition related to an automotive body performance of the automotive body model, a constraint condition related to a volume of the automotive body model and a loading condition to be imposed on the automotive body model; and obtain sensitivities of respective elements that satisfies the objective condition under the loading condition and the constraint condition; and automotive body parts sensitivity calculating unit configured to calculate sensitivities of each of the automotive body parts based on the sensitivities of the respective elements.

Moreover, in the apparatus for analyzing sensitivity of the automotive body parts according to the present invention, the sensitivity analyzing unit is configured to: calculate material densities of the respective elements satisfying the objective condition; and set the calculated material densities of the respective elements as the sensitivities of the respective elements.

Moreover, in the apparatus for analyzing sensitivity of the automotive body parts according to the present invention, the sensitivity analyzing unit is configured to standardize values of the calculated sensitivities of each of the automotive body parts, to values between 0 and 1.

Moreover, in the apparatus for analyzing sensitivity of the automotive body parts according to the present invention, the elements in the automotive body model acquiring unit are shell elements, and the automotive body parts sensitivity calculating unit is configured to: obtain a sensitivity per element area by dividing the sensitivity of the respective elements by an area of the respective elements; and set an integrated value obtained by adding up the sensitivity per element area for each of the automotive body parts or a value obtained by dividing the integrated value by number of elements included in each of the automotive body parts, as the sensitivity of each of the automotive body parts.

Moreover, in the apparatus for analyzing sensitivity of the automotive body parts according to the present invention, the elements in the automotive body model acquiring unit are rectangular elements, and the area of the element in the automotive body parts sensitivity calculating unit is obtained by: dividing each of the rectangular elements into two triangles each having three of the four nodal points of the rectangular element as vertices; calculating an area of each of the divided triangles; and taking a sum of the calculated areas of each of the divided triangles.

Moreover, in the apparatus for analyzing sensitivity of the automotive body parts according to the present invention, the elements in the automotive body model acquiring unit are rectangular elements, and the area of the element in the automotive body parts sensitivity calculating unit is obtained by: dividing each of the rectangular elements into four triangles each having a center of gravity and two adjacent nodal points as vertices; calculating an area of each of the divided triangles; and taking a sum of the calculated areas of each of the divided triangles.

Moreover, in the apparatus for analyzing sensitivity of the automotive body parts according to the present invention, the automotive body parts sensitivity calculating unit is configured to set a highest sensitivity of the sensitivities of the elements making up each of the automotive body parts as a sensitivity of the each of the automotive body parts.

Advantageous Effects of Invention

In the present invention, a computer analyzes, related to an automotive body performance of the automotive body including a plurality of automotive body parts, a sensitivity of each of the automotive body parts. The analyzing includes: an automotive body model acquisition step for acquiring an automotive body model including the automotive body parts modelled with a plurality of elements; a sensitivity analysis step for setting an objective condition related to the automotive body performance of the automotive body model, a constraint condition related to a volume of the automotive body model, and a condition of a load imposed on the automotive body model, and for obtaining the sensitivities of the respective elements, the sensitivities satisfying the objective condition under the load condition and the constraint condition; and an automotive body parts sensitivity calculating step for calculating the respective sensitivities of the automotive body parts based on the sensitivities of the respective elements, whereby it is possible to calculate a sensitivity of each of the automotive body parts to the automotive body performance, so that it becomes possible to accurately select the automotive body part to be provided with a measure for improving the automotive body performance, and to contribute to an improvement of the automotive body performance and a weight reduction.

BRIEF DESCRIPTION OF DRAWINGS

FIG. 4 is a distribution map ((a) a perspective view and (b) a bottom view) of material densities of respective elements calculated by the sensitivity analyzing unit in the first embodiment of the present invention.

FIG. 7 is a distribution map ((a) a perspective view and (b) a bottom view) of sensitivities calculated for the respective automotive body parts in the first embodiment of the present invention.

FIG. 8 is a distribution map ((a) a perspective view and (b) a bottom view) in which values of the sensitivities calculated for the respective automotive body parts are standardized, in the first embodiment of the present invention.

FIG. 10 is a stress distribution ((a) a perspective view and (b) a bottom view) resultant of applying a load condition of a static torsion (static torsion) to the automotive body model, in an example of the present invention.

FIG. 12 is a distribution map ((a) a perspective view and (b) a bottom view) of the sensitivities of the respective automotive body parts calculated by giving a load condition of a static torsion to the automotive body model, in the example of the present invention.

FIG. 13 is a distribution map ((a) a perspective view and (b) a bottom view) of the material densities of the respective elements calculated by giving a load condition of a torsion to the automotive body model using an inertia relief method, in the example of the present invention.

FIG. 14 is stress distributions ((a) a perspective view and (b) a bottom view) resultant of applying a load condition of a torsion to the automotive body model using the inertia relief method in the example of the present invention.

DESCRIPTION OF EMBODIMENTS

Before a first embodiment and a second embodiment of the present invention is explained, an automotive body that is a subject of the present invention will now be explained.

Automotive Body

An automotive body that is a subject of the present invention includes a plurality of automotive body parts, and examples of the automotive body parts include automotive body frame parts such as a dash panel, and main floor parts, undercarriage parts such as suspension parts, and steering support parts supporting the steering wheel directly or indirectly.

First Embodiment

Sensitivity Analysis Apparatus for Automotive Body Parts

A configuration of a sensitivity analysis apparatus for automotive body parts according to the first embodiment of the present invention (hereinafter, simply referred to as a "sensitivity analysis apparatus") will now be explained.

Figure 1:
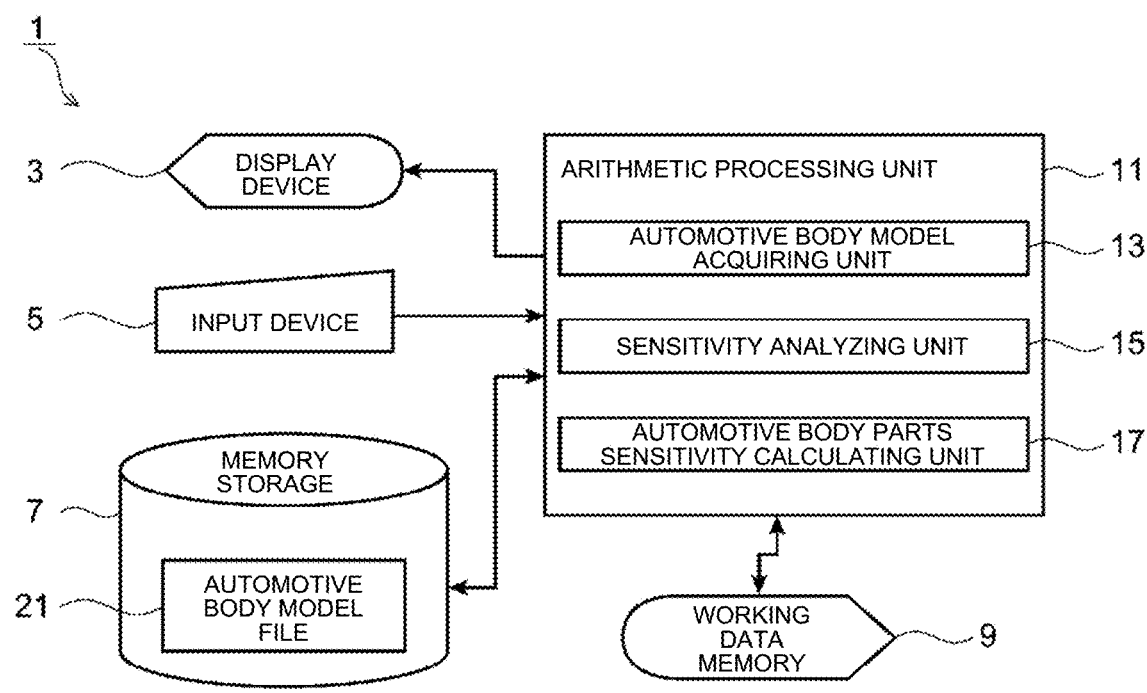
FIG. 1 is a block diagram of a sensitivity analysis apparatus for automotive body parts, according to a first embodiment of the present invention.

The sensitivity analysis apparatus 1 according to an embodiment is provided with a personal computer (PC) and the like, as illustrated in FIG. 1, and includes a display device 3, an input device 5, a memory storage 7, a working data memory 9, and an arithmetic processing unit 11. The display device 3, the input device 5, the memory storage 7, and the working data memory 9 are connected to the arithmetic processing unit 11, and each of these functions is executed in response to an instruction of the arithmetic processing unit 11.

The elements of the sensitivity analysis apparatus 1 according to the embodiment will now be explained, for a case of calculating a sensitivity of each automotive body parts included in an automotive body model 31 illustrated in FIG. 2, using the automotive body model 31 as the target of the analysis.

Display Device

The display device 3 is used for displaying analysis results, for example, and includes a liquid crystal monitor, for example.

Input Device

The input device 5 is used for giving an instruction of displaying or for entering conditions to an automotive body model file 21, for example, and includes a keyboard and a mouse, for example.

Memory Storage

The memory storage 7 is used for storing various files, such as an automotive body model file 21 storing therein various types of information related to an automotive body model, as will described later, for example, and includes a hard disk, for example.

Working Data Memory

The working data memory 9 is used for temporarily storing therein data used by the arithmetic processing unit 11, and for its arithmetic operations, and includes a random access memory (RAM), for example.

Arithmetic Processing Unit

The arithmetic processing unit 11 includes, as illustrated in FIG. 1, an automotive body model acquiring unit 13, a sensitivity analyzing unit 15, and automotive body parts sensitivity calculating unit 17, and includes a central processing unit (CPU) on a PC or the like. These units function by causing the CPU to execute a predetermined computer program. Functions of the units included in the arithmetic processing unit 11 will now be explained.

Automotive Body Model Acquiring Unit

Figure 2:
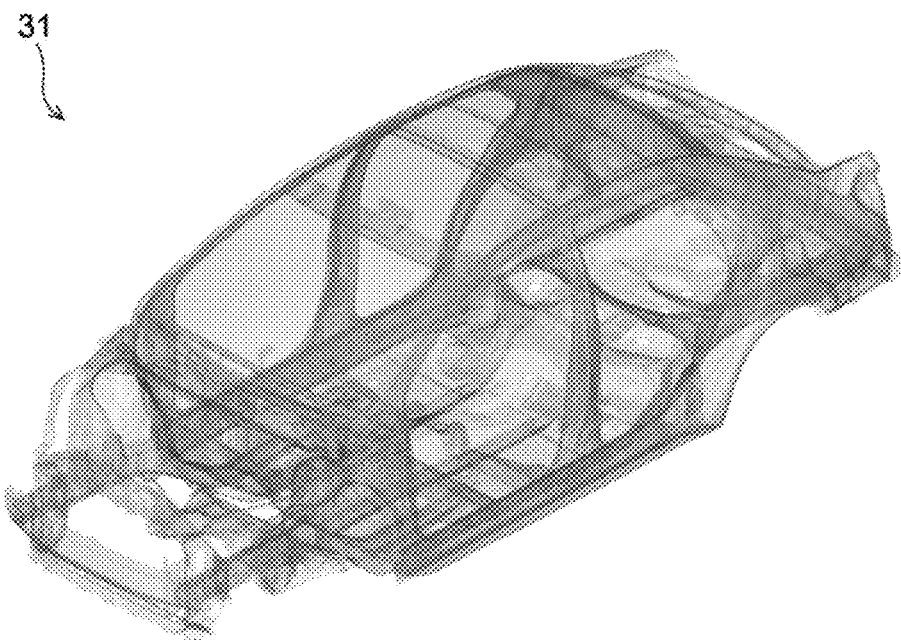
FIG. 2 is a schematic illustrating an automotive body model to be analyzed in the first embodiment of the present invention.

The automotive body model acquiring unit 13 is configured to acquire the automotive body model 31 including the automotive body parts each modelled with a plurality of elements, as illustrated in FIG. 2.

In the present embodiment, it is assumed that the automotive body parts included in the automotive body model 31 are modelled using shell elements, and information related to the shell elements making up each of the automotive body parts, and their material properties (such as Young's modulus, specific gravity, and Poisson's ratio) are recorded in the automotive body model file 21 stored in the memory storage 7 (see FIG. 1). Therefore, by reading the automotive body model file 21, the automotive body model acquiring unit 13 can acquire the automotive body model 31.

Sensitivity Analyzing Unit

The sensitivity analyzing unit 15 is configured to set an objective condition related to the automotive body performance of the automotive body model 31, a constraint condition related to the volume of the automotive body model 31, and a load condition imposed on the automotive body model 31, and to obtain a sensitivity of each element, the sensitivity satisfying the objective condition under the load condition and the constraint condition. As the sensitivity of the element, a material density of the element is calculated.

In the present embodiment, examples of the objective condition set by the sensitivity analyzing unit 15 include minimization of the sum of the strain energy, minimization of the displacement, minimization of the stress, and maximization of the stiffness, in the automotive body model 31. Furthermore, an example of the constraint condition set by the sensitivity analyzing unit 15 includes a volume constraint fraction defining the volume of the automotive body part.

Figure 3:
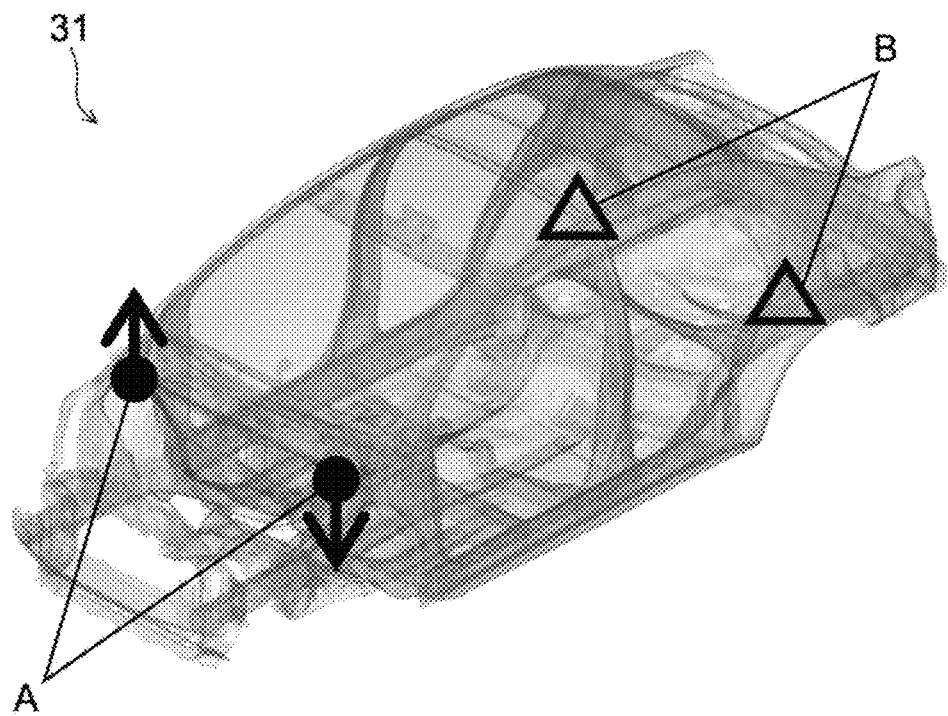
FIG. 3 is a schematic illustrating one example of conditions of loads (load/constraint) imposed on the automotive body model in a sensitivity analysis performed by a sensitivity analyzing unit in the first embodiment of the present invention.

The sensitivity analyzing unit 15 sets the load/constraint illustrated in FIG. 3, for example, as a load condition imposed on the automotive body model 31. In the load/constraint illustrated in FIG. 3, an upward load is imposed, in a vertical direction, on one of the positions where the front suspensions are mounted (A in FIG. 3) in the automotive body model 31, and a downward load is imposed in the vertical direction on the other, and constraints are given to positions where the rear sub-frame is mounted on the automotive body model 31 (B in FIG. 3).

The material density of an element calculated by the sensitivity analyzing unit 15 corresponds to, when the density method is used in the topology optimization, a density ρ in following Equation (1).

$$F = \rho K x \quad (1)$$

F: Load Vector
ρ: Standardized Density
K: Stiffness Matrix
x: Displacement Vector The standardized density ρ in Equation (1) is a virtual density representing the degree by which the material is filled in each of the elements, and takes a value between 0 and 1. In other words, when the material density of the element is 1, the element is completely filled with the material, and when the material density is 0, the element is not filled with the material at all and is completely hollow. When the material density of the element is a value in between 0 and 1, the element exhibits an in-between condition that cannot be determined as to be filled with the material or to be hollow.

In the material densities calculated through the topology optimization analysis, the material density of an element takes a value closer to one when the element contributes greatly to the automotive body performance, and such a value indicates that the sensitivity to the automotive body performance is high. By contrast, the material density of an element contributing less to the automotive body performance takes a value closer to zero, and indicates that the sensitivity to the automotive body performance is low. In this manner, the material density of the element calculated through the topology optimization analysis serves as an index representing the sensitivity of each element to the automotive body performance.

As one example of the sensitivity of an element calculated by the sensitivity analyzing unit 15, FIG. 4 illustrates one example of element material densities resultant of setting the objective condition to the maximum stiffness, and setting the constraint condition to a volume constraint ratio of 25%, and by imposing a static torsion onto the automotive body model 31, in the load/constraint conditions illustrated in FIG. 3. In FIG. 4, the values of the element material densities are high near where the front suspensions are mounted, across the floor area, and near the C pillars, and it can be seen that these elements are highly sensitive to the automotive body performance.

The sensitivity analyzing unit 15 may also set a load condition taking an inertial force caused by a dynamic torsion imposed on the automotive body model 31 into consideration, using an inertia relief method. An inertia relief method is an approach for analysis in which a stress and a strain are calculated based on the forces acting on an object going through a uniformly accelerated motion, in a condition where the object is supported at a support point serving as the reference coordinate of the inertial force (free support state), and is used in static analysis of an airplane or a ship in motion.

When the sensitivity analyzing unit 15 is caused to calculate the element material densities, it is possible to use commercially available analysis software that executes optimization processes such as the topology optimization. When this is the case, the material densities that are equivalent to the sensitivities of the respective elements are calculated by establishing each of the automotive body parts included in the automotive body model 31 as a design space, by giving a material density to an element making up the automotive body part established as a design space as a design variable, and by setting a predetermined objective condition, and constraint condition, and load condition.

When the sensitivity analyzing unit 15 is caused to perform an optimization analysis process, it is possible to use a calculation method other than the topology optimization, and the sensitivity analyzing unit 15 may also be configured to execute, as the optimization analysis process, commercially available analysis software that uses a finite element method, for example.

Automotive Body Parts Sensitivity Calculating Unit

The automotive body parts sensitivity calculating unit 17 is configured to calculate the sensitivity for each of the automotive body parts, based on the sensitivities of the respective elements calculated by the sensitivity analyzing unit 15.

In the present embodiment, it is assumed that the automotive body parts are modelled with shell elements, and the sensitivity of each of the automotive body parts is calculated in accordance with the following steps.

To begin with, a sensitivity per element area is calculated for each shell element, by dividing the sensitivity of the shell element calculated by the sensitivity analyzing unit 15 by the area of the shell element. The sensitivities per respective element areas are then added up for each of the automotive body parts to obtain a sum. As a result, the thus obtained sum can be set as the sensitivity of each of the automotive body parts. The sum of the sensitivities per element area for the corresponding automotive body part may also be divided by the number of elements included in the automotive body part to obtain a calculated value, and the calculated value may be set as the sensitivity of the automotive body part.

When the sensitivities of the respective automotive body parts are compared to one another, because the sensitivities are affected not only by the difference in the areas of the automotive body parts but also by the sizes of the shell elements, dividing the sensitivity per element area by the number of elements for standardization allows the sensitivities of the respective automotive body parts to be compared one another.

The element area of a shell element can be calculated using nodal coordinates. When triangular elements are used as the shell elements, the element area of a triangular element can be calculated by calculating the outer product or the like, from the coordinates of the three nodal points of the triangular element.

When a rectangular element is used as the shell element, the element area of the rectangular element can be also calculated from four nodal coordinates of the rectangular element. For example, when the four nodal points $N_1$ to $N_4$ are located on the same plane like a rectangular element 41 in FIG. 5(a) (on the XY plane in FIG. 5(a)), the element area of each of the rectangular element can be calculated by calculating the position of an intersection P of two diagonals $L_1$ and $L_2$, and by dividing the area into four triangles ($PN_1N_2$, $PN_2N_3$, $PN_3N_4$, and $PN_4N_1$) each of which is delineated by the intersection P and adjacent two nodal points of the rectangular element.

Figure 5:
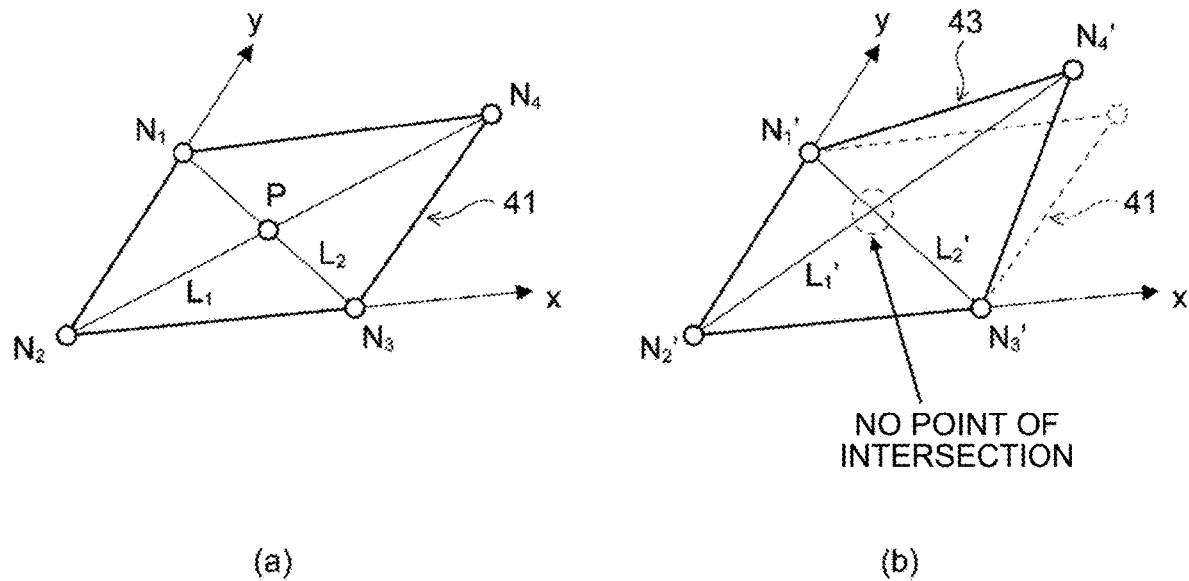
FIG. 5 is a schematic for explaining the issues in calculating the area of an element when rectangular elements are used in the modelling of an automotive body part in the first embodiment of the present invention.

However, when a rectangular element 43 is twisted and the four nodal points $N_1'$ to $N_4'$ are not on the same plane (the XY plane in FIG. 5(b)) as illustrated in FIG. 5(b), because the two diagonals $L_1'$ and $L_2'$ do not intersect with each other, it is not possible to calculate the intersection of the diagonals as it is for the rectangular element 41 described above, and therefore, it is not possible to calculate the area of the rectangular element 43.

Therefore, in the present embodiment, when rectangular elements (with four nodal points) are used as the shell elements, the element area is calculated in accordance with a step (a) or (b) described below.

Figure 6:
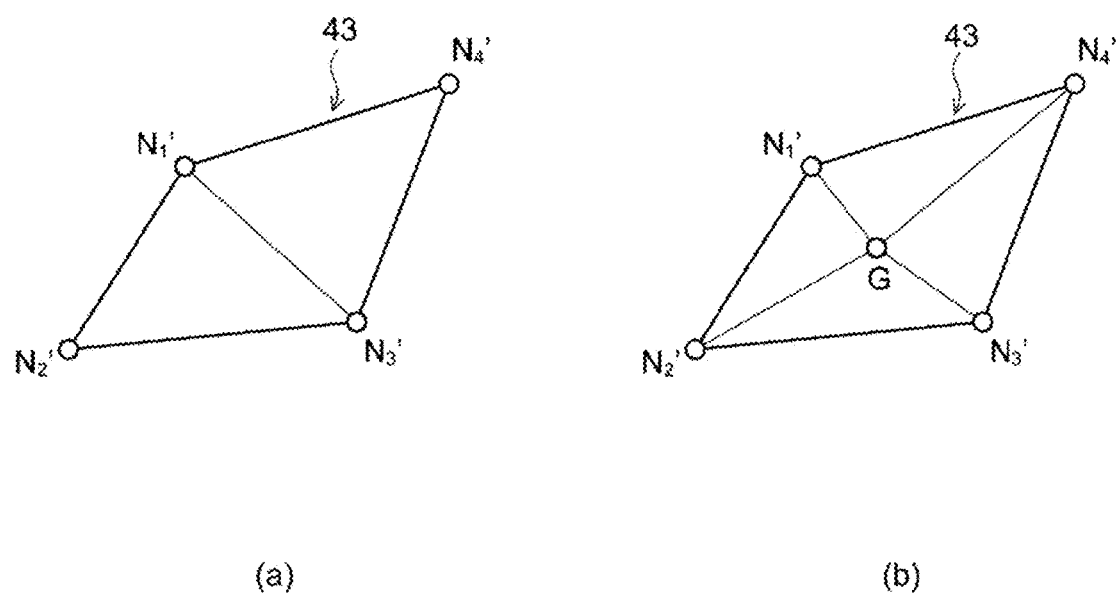
FIG. 6 is a schematic for explaining a method for calculating the area of the rectangular element used in the modelling of an automotive body part in the first embodiment of the present invention.

(a) As illustrated in FIG. 6(a), the rectangular element is divided into two triangles one of which is a triangle ($N_1'N_2'N_3'$) having three of the four nodal points of the rectangular element as its vertices, and another triangle ($N_4'N_1'N_3'$) including the remaining one of the nodal points. The area of each of the divided triangles is then calculated, and the sum of these areas is used as the element area of the rectangular element.

(b) As illustrated in FIG. 6(b), the position of the center of gravity G of the rectangular element 43 is calculated, and the rectangular element is divided into four triangles ($GN_1'N_2'$, $GN_2'N_3'$, $GN_3'N_4'$ and $GN_4'N_1'$) each having the center of gravity G and adjacent two of the nodal points as vertices. The area of each of the divided triangles is then calculated, and the sum of these areas is used as the element area of the rectangular element.

By taking the step (a) or (b) described above, it is possible to calculate the area even when the rectangular element 43 is twisted.

FIG. 7 illustrates one example of the sensitivities of the respective automotive body parts when the sensitivity per element area is calculated using the area of the rectangular elements, following the step (a) described above.

In the manner described above, the automotive body parts sensitivity calculating unit 17 can calculate sensitivities for the respective automotive body parts. To display the sensitivities of the respective automotive body parts on the automotive body model 31 as a distribution map, the automotive body parts sensitivity calculating unit 17 may standardize the calculated sensitivities of the respective automotive body parts in such a manner that the sensitivities fall within the range between 0 and 1 as illustrated in FIG. 8.

Sensitivity Analysis Method for Automotive Body Parts

A sensitivity analysis method for automotive body parts (hereinafter, simply referred to as a "sensitivity analysis method") according to the embodiment will now be explained.

Figure 9:
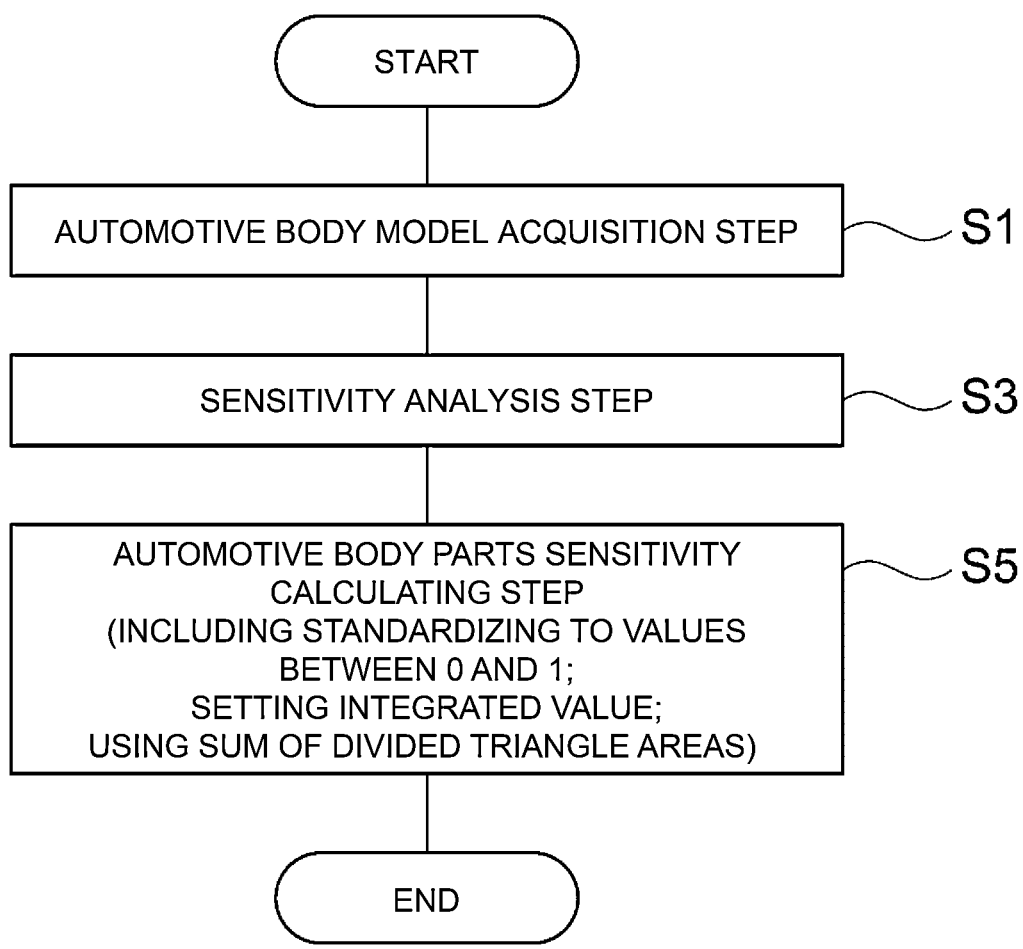
FIG. 9 is a schematic illustrating the sequence of a process of a sensitivity analysis method for automotive body parts according to the first embodiment of the present invention.

The sensitivity analysis method according to the embodiment is intended to cause a computer to analyze the sensitivities of automotive body parts to an automotive body performance of an automotive body having a plurality of the automotive body parts, and includes, as illustrated in FIG. 9, an automotive body model acquisition step S1, a sensitivity analysis step S3, and an automotive body parts sensitivity calculating step S5, and these steps are executed by the sensitivity analysis apparatus 1 implemented as a computer (see FIG. 1). Each of the steps described above will now be explained.

Automotive Body Model Acquisition Step

The automotive body model acquisition step S1 is a step for acquiring the automotive body model 31 (see FIG. 2) including the automotive body parts modelled with a plurality of elements. In the present embodiment, the automotive body model acquiring unit 13 in the sensitivity analysis apparatus 1 acquires the automotive body model 31 including the automotive body parts modelled with a plurality of shell elements by reading the automotive body model file 21 (see FIG. 1).

Sensitivity Analysis Step

The sensitivity analysis step S3 is a step for setting an objective condition related to the automotive body performance of the automotive body model 31, a constraint condition related to the volume of the automotive body model 31, and a condition of the load imposed on the automotive body model, and calculating the sensitivities of the elements satisfying the objective condition under such a constraint condition. In the present embodiment, the sensitivity analyzing unit 15 of the sensitivity analysis apparatus 1 sets an objective condition, a constraint condition, and a load condition, and calculates the material densities of the elements, as the sensitivities of the respective elements.

At the sensitivity analysis step S3, an optimization analyzing process such as the topology optimization may also be performed. When this is the case, one of the automotive body parts included in the automotive body model 31 is established as a design space, and an optimization analyzing process is performed by giving material density to each of the elements included in the automotive body part established as the design space, as the design variables. In this manner, the material density satisfying the objective condition under the set constraint condition and load condition can then be calculated for each of the elements.

Automotive Body Parts Sensitivity Calculating Step

The automotive body parts sensitivity calculating step S5 is a step for calculating the sensitivity of each of the automotive body parts based on the sensitivities of the elements calculated at the sensitivity analysis step S3. In the present embodiment, the automotive body parts sensitivity calculating unit 17 in the sensitivity analysis apparatus 1 calculates a sensitivity per element area by dividing the material density of each of the elements, which is calculated by the sensitivity analyzing unit 15, by the area of the element, adds up the sensitivities per respective element areas for each of the automotive body parts to obtain a sum, and calculates the sensitivity of each of the automotive body parts. The sum calculated for each of the automotive body parts may be divided by the number of elements included in the automotive body part, as the sensitivity of the automotive body part.

At the automotive body parts sensitivity calculating step S5, the calculated values of the sensitivities of the respective automotive body parts may be standardized, so as to display the sensitivities of the automotive body parts on the automotive body model 31 as a distribution map, as illustrated in FIG. 8, in such a manner that the values fall within the range between 0 and 1.

With the method and apparatus for analyzing sensitivity of automotive body parts according to the embodiment, it is possible to calculate a sensitivity of each of the automotive body parts with respect to the automotive body performance, so that it becomes possible to accurately select an automotive body part where a measure for improving the automotive body performance is to be provided.

Furthermore, with the method and apparatus for analyzing sensitivity of automotive body parts according to the embodiment, by selecting the automotive body part with a high sensitivity to the automotive body performance, it is possible to perform a shape optimization analysis such as a topology optimization to such an automotive body part, efficiently, and to further contribute to the improvement of the automotive body performance and to a weight reduction of the automotive body.

In the explanation above, the automotive body performance is intended to improve the stiffness of the automotive body, but to improve crashworthiness or durability as the automotive body performance, an objective condition related to the crashworthiness or the durability may be set at the sensitivity analyzing unit or sensitivity analysis step.

Furthermore, for the sensitivity analyzing unit and the sensitivity analysis step explained above, a material density is calculated for each of the elements as the sensitivity of the element, but according to the present invention, when automotive body parts are modelled with a plurality of shell elements, the thickness of each of the shell elements satisfying a predetermined objective condition, constraint condition, and load condition may be calculated, and the calculated thickness of the shell element may be set as the sensitivity of the element.

In the sensitivity analysis, when the thickness of each of the shell elements is calculated, an element with a greater thickness represents a higher sensitivity to the automotive body performance, and an element with a smaller thickness represents a lower sensitivity to the automotive body performance. In this manner, the thickness of the element calculated in the sensitivity analysis can serve as an index representing the sensitivity of the element to the automotive body performance.

In the explanation above, the automotive body parts included in the automotive body model are explained to be modelled with a plurality of shell elements, but the present invention is not limited to the automotive body parts modelled with shell elements, but may be intended for the automotive body parts modelled with a plurality of three-dimensional elements, or those modelled with a plurality of shell elements and three-dimensional elements.

For the automotive body parts modelled with three-dimensional elements, when the sensitivity for each of the automotive body parts is calculated, a sensitivity per element volume, instead of the element area, may be used, by dividing the sensitivity obtained for each of the three-dimensional elements by an element volume of the three-dimensional element.

Furthermore, according to the present invention, at the automotive body parts sensitivity calculating unit or the automotive body parts sensitivity calculating step, out of the sensitivities of the elements making up each of the automotive body parts, the highest sensitivity thereof may be a sensitivity of the automotive body part.

Second Embodiment

A material property determination method for automotive body parts according to a second embodiment of the present invention uses the sensitivity analysis method for automotive body parts according to the first embodiment, and determines the material property of each of the automotive body parts, based on the sensitivity acquired for each of the automotive body parts.

Some examples of the material property of an automotive body part include Young's modulus, a specific gravity, and Poisson's ratio. The material property can be determined for each of the automotive body parts such that, for example, an automotive body part determined to have a high sensitivity is judged as a material with high Young's modulus, and an automotive body part determined to have a lower sensitivity as a lightweight material with low Young's modulus. In this manner, it is possible to efficiently improve the automotive body performance.

EXAMPLE

Some experiments have been carried out to verify the advantageous effects of the sensitivity analysis method and apparatus for an automotive body parts according to the present invention, so these experiment results will now be explained.

In this example, to begin with, the automotive body model 31 illustrated in FIG. 2 was acquired. The automotive body model 31 included automotive body parts modelled with a plurality of shell elements (rectangular elements). A sensitivity analysis was then carried out by giving an objective condition related to the automotive body performance, a constraint condition to the volume of the automotive body model, and a condition of a load imposed on the automotive body model, and a material density was calculated for each of the elements, as the sensitivity of the element satisfying the objective condition under the load condition and the constraint condition. In the present embodiment, the sensitivities per respective element areas is added up for each of the automotive body parts to obtain a sum, and the sum was divided by the number of elements in the automotive body part to obtain a result as the sensitivity of the automotive body part. The sensitivity for each of the automotive body parts is then calculated based on the calculated material density of the elements. The sensitivity of each of the automotive body parts was then standardized in such a manner that the values fall within a range between 0 and 1 across the entire automotive body model 31.

FIG. 8 mentioned earlier illustrates a result of displaying the sensitivities of the respective automotive body parts as a distribution map on the automotive body model 31, the sensitivities being calculated using the sensitivity analysis method for an automotive body parts according to the present invention. To enable a comparison, FIG. 4 mentioned above illustrates a result of mapping the material densities of the respective elements as a distribution map onto the automotive body model 31, the material densities being calculated by the sensitivity analysis.

In the material densities corresponding to the respective elements illustrated in FIG. 4, because even the same automotive body part has some high material densities and low material densities, it is not possible to determine which automotive body part has a sensitivity higher than the sensitivity of the entire automotive body to the automotive body performance. By contrast, in the result of the sensitivity calculation of the automotive body parts illustrated in FIG. 8, the automotive body part with a higher sensitivity to the automotive body performance is clearly presented, and, under the conditions according to this example, it can be seen that the sensitivity is the highest near the positions where the front suspensions are mounted, and also the dash panel and the main floor parts have high sensitivities.

FIG. 10 illustrates a stress distribution in the automotive body model 31 when the load/constraint conditions illustrated in FIG. 3 are given as the load condition imposed on the automotive body model 31. Based on FIG. 10, although a higher stress is exhibited near the positions where the front suspensions are mounted, it can be seen that, in comparison with the sensitivities of the respective automotive body parts illustrated in FIG. 8, the positions of high-stress parts do not necessarily match the high-sensitivity automotive body parts in the automotive body model 31. Based on this, it can be understood that it is more difficult to select an automotive body part having a higher sensitivity to the automotive body performance, based on the result of the stress.

Figure 11:
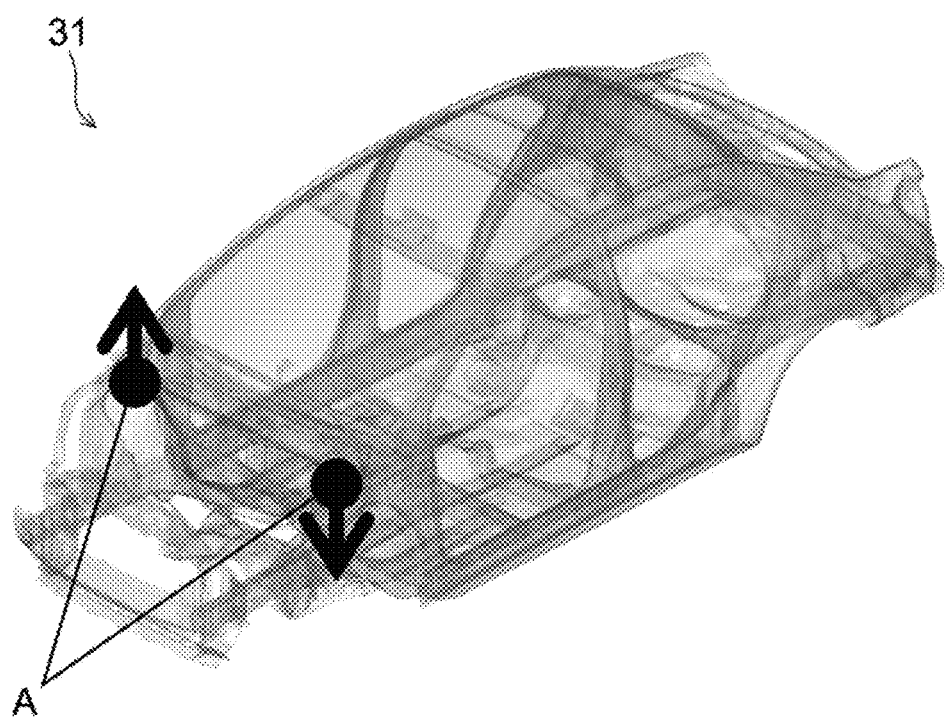
FIG. 11 is a schematic illustrating a load condition of a torsion applied to the automotive body model using an inertia relief method in the example of the present invention.

Furthermore, in this example, the sensitivities of the automotive body parts were also calculated using a load condition taking the inertial force of the automotive body into account, with the inertia relief method, as illustrated in FIG. 11.

FIG. 12 illustrates a result in which the sensitivities calculated for the respective automotive body parts using the sensitivity analysis method for automotive body parts according to the present invention are displayed on the automotive body model 31, as a distribution map. To enable a comparison, the element material densities resultant of calculating by giving the load condition illustrated in FIG. 11 to the automotive body model 31 are illustrated in FIG. 13, and the result of the stress distribution in the automotive body model 31 is illustrated in FIG. 14.

It is implied that, based on the result of material densities of the respective elements illustrated in FIG. 13 and the result of the stress distribution of the elements illustrated in FIG. 14, the front part of the automotive body model 31 has a higher sensitivity to the automotive body performance, but it cannot be determined which automotive body part has a high sensitivity. By contrast, based on the result of the sensitivities of the respective automotive body parts illustrated in FIG. 12, obtained is a result in which the order of the automotive body parts having more significant sensitivities to the automotive body performance become apparent.

Based on the results described above, with the sensitivity analysis method and apparatus for automotive body parts according to the present invention, it has been indicated that it is possible to clearly identify an automotive body part where a measure for improving the automotive body performance is to be provided.

INDUSTRIAL APPLICABILITY

In the present invention, it is possible to provide a method and apparatus for analyzing a sensitivity of automotive body parts, and a method for determining material property method of automotive body parts that are able to analyze the sensitivity of each of the automotive body parts with respect to the automotive body performance, and of clarify the automotive body part where a measure for improving the automotive body performance is to be provided.

REFERENCE SIGNS LIST 1 sensitivity analysis apparatus
3 display device
5 input device
7 memory storage
9 working data memory
11 arithmetic processing unit
13 automotive body model acquiring unit
15 sensitivity analyzing unit
17 automotive body parts sensitivity calculating unit
21 automotive body model file
31 automotive body model
41 rectangular element
43 rectangular element

The invention claimed is:

1. A computer-aided engineering (CAE) analyzing method executed by a computer for designing an automotive body by a topology optimization of determining automotive body parts that contributes to a performance of the automotive body and setting a design space based on the determined automotive body parts, the method comprising:
analyzing sensitivities of the automotive body parts with respect to the automotive body performance of the automotive body by:
acquiring an automotive body model including the automotive body parts modeled with shell elements;
setting:
an objective condition related to the automotive body performance of the automotive body model;
a constraint condition related to a volume of the automotive body model; and
a loading condition to be imposed on the automotive body model;
obtaining the sensitivities of respective shell elements that satisfy the objective condition under the loading condition and the constraint condition; and
calculating the sensitivities of each of the automotive body parts based on the sensitivities of the respective shell elements, for selecting the automotive body part with a highest sensitivity to the automotive body performance as the design space for the CAE analysis for the automotive body by the topology optimization, wherein
the obtaining includes:
calculating material densities of the respective shell elements satisfying the objective condition by using a density method of the topology optimization; and
setting the calculated material densities of the respective shell elements as the sensitivities of the respective shell elements, wherein the material densities of the respective shell elements are output to a display as the sensitivities of the respective shell elements, and
the sensitivities of each of the automotive body parts are output to the display as a distribution map.

2. The method according to claim 1, wherein the calculating of the sensitivities includes standardizing values of the calculated sensitivities of each of the automotive body parts, to values between 0 and 1.

3. The method according to claim 1, wherein
the calculating of the sensitivities includes:
obtaining a sensitivity per element area by dividing the sensitivity of the respective shell elements by an area of the respective shell elements; and
setting an integrated value obtained by adding up the sensitivity per element area for each of the automotive body parts or a value obtained by dividing the integrated value by the number of shell elements included in each of the automotive body parts, as the sensitivity of each of the automotive body parts.

4. The method according to claim 3, wherein
the shell elements are rectangular elements, and
at the calculating of the sensitivities, the area of the respective shell elements is obtained by:
dividing each of the rectangular elements into two triangles each having three of the four nodal points of the rectangular element as vertices;
calculating an area of each of the divided triangles; and
taking a sum of the calculated areas of each of the divided triangles.

5. The method according to claim 3, wherein
the shell elements are rectangular elements, and
at the calculating of the sensitivities, the area of the respective shell elements is obtained by:
dividing each of the rectangular elements into four triangles each having a center of gravity and two adjacent nodal points of the rectangular element as vertices;
calculating an area of each of the divided triangles; and
taking a sum of the calculated areas of each of the divided triangles.

6. The method according to claim 1, wherein, at the calculating of the sensitivities, the highest sensitivity of the sensitivities of the shell elements making up each of the automotive body parts is set as the sensitivity of each of the automotive body parts.

7. An apparatus for computer-aided engineering (CAE) analyzing for designing an automotive body by a topology optimization of determining automotive body parts that contributes to a performance of the automotive body and setting a design space based on the determined automotive body parts, the apparatus comprising:
a hardware processor programmed to analyze sensitivities of the automotive body parts with respect to the automotive body performance of the automotive body by:
acquiring an automotive body model including the automotive body parts modeled with shell elements;
setting:
an objective condition related to the automotive body performance of the automotive body model;
a constraint condition related to a volume of the automotive body model; and
a loading condition to be imposed on the automotive body model;
obtaining the sensitivities of respective shell elements that satisfy the objective condition under the loading condition and the constraint condition; and
calculating the sensitivities of each of the automotive body parts based on the sensitivities of the respective shell elements, for selecting the automotive body part with a highest sensitivity to the automotive body performance as the design space for the CAE analysis for the automotive body by the topology optimization, wherein the processor is programmed, when obtaining the sensitivities, to:
  calculate material densities of the respective shell elements satisfying the objective condition by using a density method of the topology optimization; and
  set the calculated material densities of the respective shell elements as the sensitivities of the respective shell elements, wherein the material densities of the respective shell elements are output to a display as the sensitivities of the respective shell elements, and
the sensitivities of each of the automotive body parts are output to the display as a distribution map.

8. The apparatus according to claim 7, wherein the processor is programmed, when calculating the sensitivities, to standardize values of the calculated sensitivities of each of the automotive body parts, to values between 0 and 1.

9. The apparatus according to claim 7, wherein
the processor is programmed, when calculating the sensitivities, to:
  obtain a sensitivity per element area by dividing the sensitivity of the respective shell elements by an area of the respective shell elements; and
  set an integrated value obtained by adding up the sensitivity per element area for each of the automotive body parts or a value obtained by dividing the integrated value by the number of shell elements included in each of the automotive body parts, as the sensitivity of each of the automotive body parts.

10. The apparatus according to claim 9, wherein
the shell elements are rectangular elements, and
the processor is programmed, when calculating the sensitivities, to obtain the area of the respective shell elements by:
  dividing each of the rectangular elements into two triangles each having three of the four nodal points of the rectangular element as vertices;
  calculating an area of each of the divided triangles; and
  taking a sum of the calculated areas of each of the divided triangles.

11. The apparatus according to claim 9, wherein
the shell elements are rectangular elements, and
the processor is programmed, when calculating the sensitivities, to obtain the area of the respective shell elements by:
  dividing each of the rectangular elements into four triangles each having a center of gravity and two adjacent nodal points as vertices;
  calculating an area of each of the divided triangles; and
  taking a sum of the calculated areas of each of the divided triangles.

12. The apparatus according to claim 7, wherein the processor is programmed, when calculating the sensitivities, to set the highest sensitivity of the sensitivities of the shell elements making up each of the automotive body parts as the sensitivity of each of the automotive body parts.

* * * * *